(12) United States Patent
Wengreen et al.

(10) Patent No.: US 9,242,108 B2
(45) Date of Patent: Jan. 26, 2016

(54) MEDICAL DEVICE SURFACE ELECTRODE

(75) Inventors: Eric John Wengreen, Stanford, CA (US); Andrew J. Ries, Lino Lakes, MN (US); David J. Saltzman, Minneapolis, MN (US); Randy S. Roles, Elk River, MN (US); Scott J. Robinson, Forest Lake, MN (US); David B. Engmark, Bethel, MN (US); John Eric Lovins, Oakdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 817 days.

(21) Appl. No.: 12/847,743

(22) Filed: Jul. 30, 2010

(65) Prior Publication Data

US 2011/0029027 A1   Feb. 3, 2011

Related U.S. Application Data

(60) Provisional application No. 61/230,537, filed on Jul. 31, 2009.

(51) Int. Cl.
*A61N 1/375* (2006.01)

(52) U.S. Cl.
CPC .............. *A61N 1/3754* (2013.01); *A61N 1/3756* (2013.01)

(58) Field of Classification Search
USPC ............................ 607/2, 36, 37; 361/302–309
See application file for complete search history.

(56) References Cited

U.S. PATENT DOCUMENTS

| | | | |
|---|---|---|---|
| 6,622,046 B2 | 9/2003 | Fraley et al. | |
| 7,019,942 B2 | 3/2006 | Gunderson et al. | |
| 7,103,408 B2 | 9/2006 | Haller et al. | |
| 7,132,173 B2 | 11/2006 | Daulton | |
| 7,493,166 B2 * | 2/2009 | Nicholson et al. | 607/36 |
| 7,749,651 B2 * | 7/2010 | Wutz et al. | 429/180 |
| 2002/0072778 A1 | 6/2002 | Guck et al. | |
| 2002/0165588 A1 | 11/2002 | Fraley et al. | |
| 2006/0217777 A1 | 9/2006 | Strom et al. | |

FOREIGN PATENT DOCUMENTS

WO    WO 2006/133444 A2    12/2006

OTHER PUBLICATIONS (PCT/US2010/044062) PCT Notification of Transmittal of the International Search Report and the Written Opinion of the International Searching Authority.

* cited by examiner

*Primary Examiner* — Erica Lee
(74) *Attorney, Agent, or Firm* — Carol F. Barry

(57) ABSTRACT

Structures and methods relating to electrodes for incorporation into a feedthrough with a profile adapted for subcutaneous sensing of physiologic and cardiac signals. Electrode assemblies are adapted for integration with feedthroughs and provide reliable insulation from the implantable medical device housing. Various structures and manufacturing processes are implemented to provide a large sensing surface with a low profile. The subcutaneous sensing electrode assembly can provide a leadless sensing system and further enhances installation and follow-up procedures.

28 Claims, 12 Drawing Sheets

MEDICAL DEVICE SURFACE ELECTRODE

CROSS-REFERENCE TO RELATED APPLICATIONS

This application claims the benefit of U.S. Provisional Application No. 61/230,537, filed on Jul. 31, 2009. The disclosure of the above application is incorporated herein by reference.

TECHNICAL FIELD

The present disclosure relates generally to implantable medical devices; and, more particularly, to securing electrodes to implantable medical devices.

BACKGROUND

Since the implantation of the first cardiac pacemaker, implantable IMD technology has advanced with the development of sophisticated implantable pulse generators (IPGs), implantable cardioverter-defibrillators (ICDs) arrhythmia control devices designed to detect arrhythmias and deliver appropriate therapies. Detection and discrimination between various arrhythmic episodes in order to trigger the delivery of an appropriate therapy is of considerable interest. Prescription for implantation and programming of the implanted device are based on the analysis of the PQRST electrocardiogram (ECG) and the electro gram (EGM). Waveforms are typically separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. Detection, analysis and storage of such EGM data within implanted medical devices are well known in the art. Acquisition and use of ECG tracing(s), on the other hand, has generally been limited to the use of an external ECG recording machine attached to the patient via surface electrodes of one sort or another.

ECG systems that detect and analyze the PQRST complex depend upon the spatial orientation and number of externally applied electrodes available near or around the heart to detect or sense the cardiac depolarization wave front. Implantable medical device systems increasingly can include communication means between implanted devices and/or an external device, for example, a programming console, monitoring system, and similar systems. For diagnostic purposes, it is desirable that the implanted device communicate information regarding the device's operational status and the patient's condition to the physician or clinician. Implantable devices can transmit or telemeter a digitized electrical signal to display electrical cardiac activity (e.g., an ECG, EGM, or the like) for storage, display and/or analysis by an external device.

To diagnose and measure cardiac events, a cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. In spite of these advances in the medical device art, the surface ECG has remained a standard diagnostic tool. A twelve-lead ECG is typically the first procedure used to determine cardiac status prior to implanting a pacing system. An ECG recording device is attached to the patient through ECG leads connected to skin electrodes arrayed on the patient's body so as to achieve a recording that displays the cardiac waveforms in any one of twelve possible vectors. An example of ECG leads with skin electrodes may be seen with respect to U.S. Pat. No. 6,622,046 to Fraley et al. issued Sep. 16, 2003, and assigned to the assignee of the present invention. Fraley et al. discloses a feed through used in combination with an electrode to sense the human body's electrical activity. It is desirable to develop new mechanical features related to securing surface ECG electrodes to the housing of an implantable medical device.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments of the present disclosure will hereinafter be described in conjunction with the appended drawings, wherein like numerals denote like elements.

DETAILED DESCRIPTION

Figure 1:
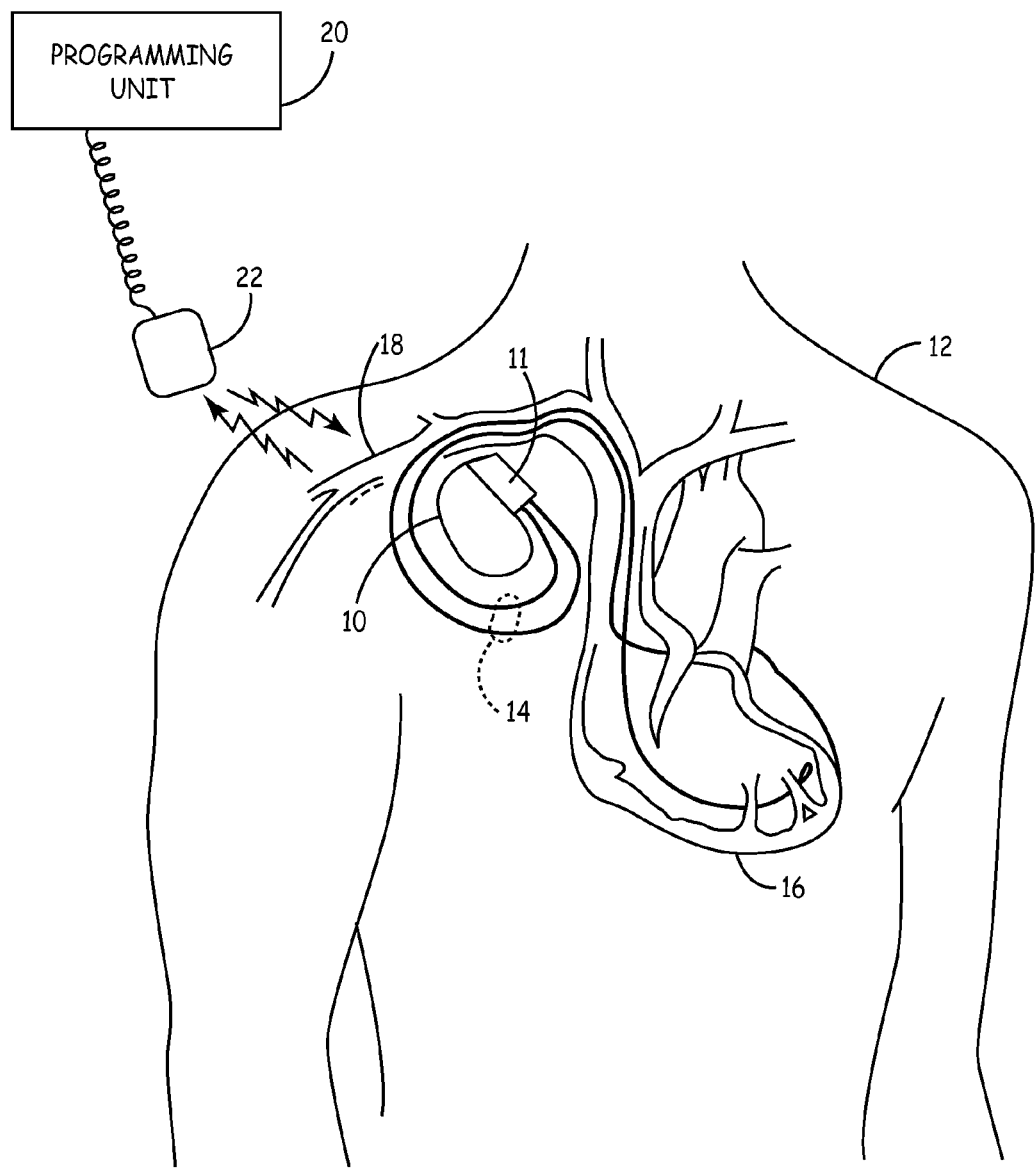
FIG. 1 is an illustration of a body-implantable device system in accordance with the present disclosure, including a hermetically sealed device implanted in a patient and an external programming unit.

The following description of the preferred embodiments is merely exemplary in nature and is in no way intended to limit the invention, its application, or uses. For purposes of clarity, similar reference numbers are used in the drawings to identify similar elements. The devices described herein include an exemplary number of leads, etc. One will understand that the components, including number and kind, may be varied without altering the scope of the disclosure. Also, devices according to various embodiments may be used in any appropriate diagnostic or treatment procedure, including a cardiac procedure.

FIG. 1 depicts an implantable medical device system adapted for use in accordance with the present disclosure. The medical device system shown in FIG. 1 includes an implantable medical device (IMD) 10 that has been implanted in patient 12. Although the present disclosure will be described herein in an embodiment which includes a pacemaker, the disclosure may be practiced in connection with numerous other types of implantable medical device systems including neurostimulators, implantable defibrillators, and insertable cardiac monitors.

In accordance with conventional practice in the art, IMD 10 is housed within a hermetically sealed, biologically inert outer housing or casing, which may comprise a metal such as titanium, stainless steel, glass, epoxy, or other suitable material. In other embodiments, the IMD housing is not hermetically sealed. One or more leads, collectively identified with reference numeral 14 in FIG. 1 are electrically coupled to IMD 10 in a conventional manner and extend into the patient's heart 16 via a vein 18. The leads 14 are joined to the IMD 10 by plugging the leads into the connector module 11. Disposed generally near the distal end of leads 14 are one or more exposed conductive electrodes for receiving electrical cardiac signals and/or for delivering electrical pacing stimuli to heart 16. Leads 14 may be implanted with their distal end(s) situated in the atrium and/or ventricle of heart 16.

Also depicted in FIG. 1 is an external programming unit 20 for non-invasive communication with IMD 10 via uplink and downlink communication channels, to be hereinafter described in further detail. Associated with programming unit 20 is a programming head 22, in accordance with conventional medical device programming systems, for facilitating two-way communication between IMD 10 and programmer 20. In many known implantable device systems, a programming head such as that depicted in FIG. 1 is positioned over the patient's body over the implant site of the device, typically within 2- to 3-inches of skin contact, such that one or more antennae within the head can send RF signals to, and receive RF signals from, an antenna disposed within the hermetic enclosure of the implanted device or disposed within the connector block of the device, in accordance with common practice in the art.

Figure 2:
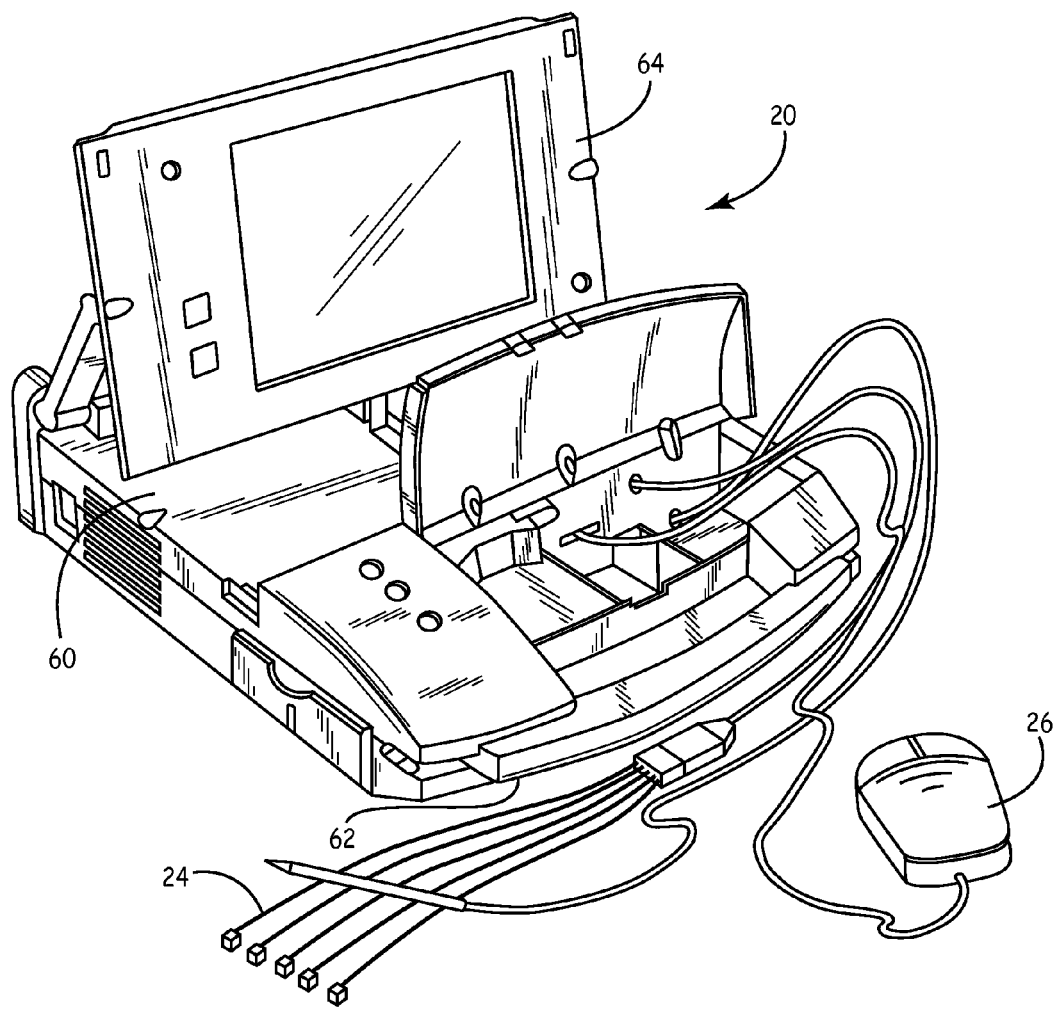
FIG. 2 is a perspective view of an exemplary external programming unit of FIG. 1.
Figure 3:
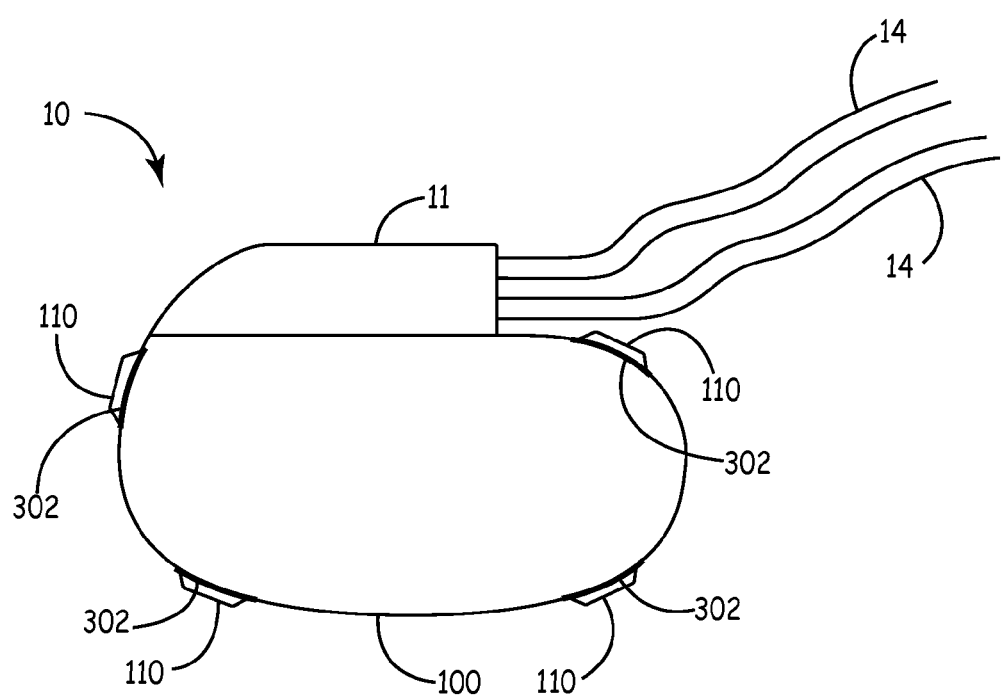
FIG. 3 is a schematic view of an implantable medical device.

FIG. 2 is a perspective view of an exemplary programming unit 20. Internally, programmer 20 includes a processing unit (not shown) that in accordance with the present disclosure is a personal computer type motherboard, e.g., a computer motherboard including an Intel Pentium 3, Intel® Core™ microprocessor or other suitable processors and related circuitry such as digital memory.

Programmer 20 comprises an outer shell 60, which is preferably made of thermal plastic or another suitably rugged yet relatively lightweight material. A carrying handle, designated generally as 62 in FIG. 2, is integrally formed into the front of outer shell 60. With handle 62, programmer 20 can be carried like a briefcase.

An articulating display screen 64 is disposed on the upper surface of outer shell 60. Display screen 64 folds down into a closed position (not shown) when programmer 20 is not in use, thereby reducing the size of programmer 20 and protecting the display surface of display 64 during transportation and storage thereof.

A disk drive is disposed within outer shell 60 and is accessible via a disk insertion slot (not shown). A hard disk drive is also disposed within outer shell 60, and it is contemplated that a hard disk drive activity indicator, (e.g., an LED, not shown) could be provided to give a visible indication of hard disk activation. In the perspective view of FIG. 2, programmer 20 is shown with articulating display screen 64.

An input device 26 such as a mouse is connected to programmer 20 which serves as an on-screen pointer in a graphical user interface presented via display screen 64. Input device 26 allows a user to input data.

To sense signals from tissue of, for example, the heart and/or deliver electrical stimuli to tissue, a low profile surface electrode assembly 110 can be connected to housing 100 of a variety of differently shaped IMDs such as IMD 10, tubular or pill-shaped IMD 150 and rectangular-shaped IMD 190 depicted in FIGS. 3 and 7-9, respectively.

Electrode assembly 110 includes an electrode with a feedthrough 150 such that feedthrough 150 secures a electrode 120 to the external surface of the housing 100 of IMD 10. An example of ECG leads with skin electrodes 120 may be seen with respect to U.S. Pat. No. 6,622,046 to Fraley et al. issued Sep. 16, 2003, and assigned to the assignee of the present invention; the disclosure of which is incorporated by reference in its entirety herein. In other embodiments (such as in FIGS. 10-14) the feedthrough does not secure the electrode to the housing. In one or more embodiments, the electrode 120 can be coated with a high surface area coating to increase the surface area of the electrode 120 without increasing the length and width of the electrode 120. For example, an electrode 120 can be coated with iridium oxide to increase the surface area.

Feedthrough 150 can be inserted or placed through the housing 100. An example of a feedthrough 150 passing through an electrode may be seen with respect to U.S. Pat. No. 6,622,046 to Fraley et al. issued Sep. 16, 2003, and assigned to the assignee of the present invention, the disclosure of which is incorporated by reference in its entirety herein.

Figure 4:
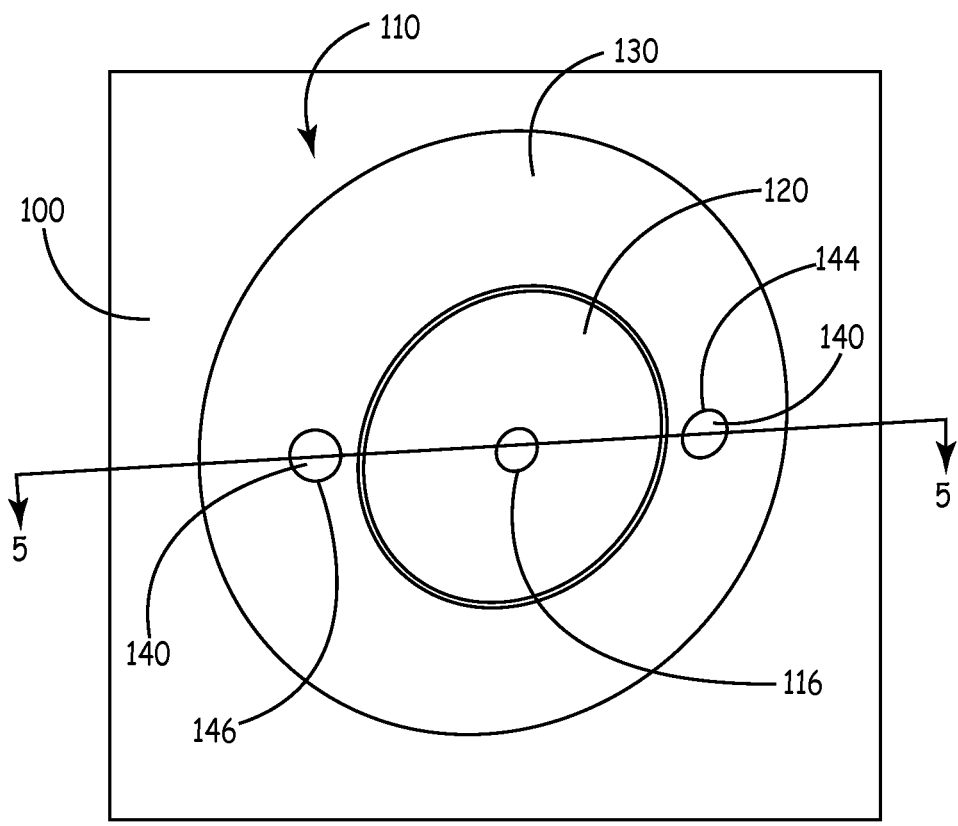
FIG. 4 is a schematic view of an exemplary electrode connected to a retention cup.
Figure 5:
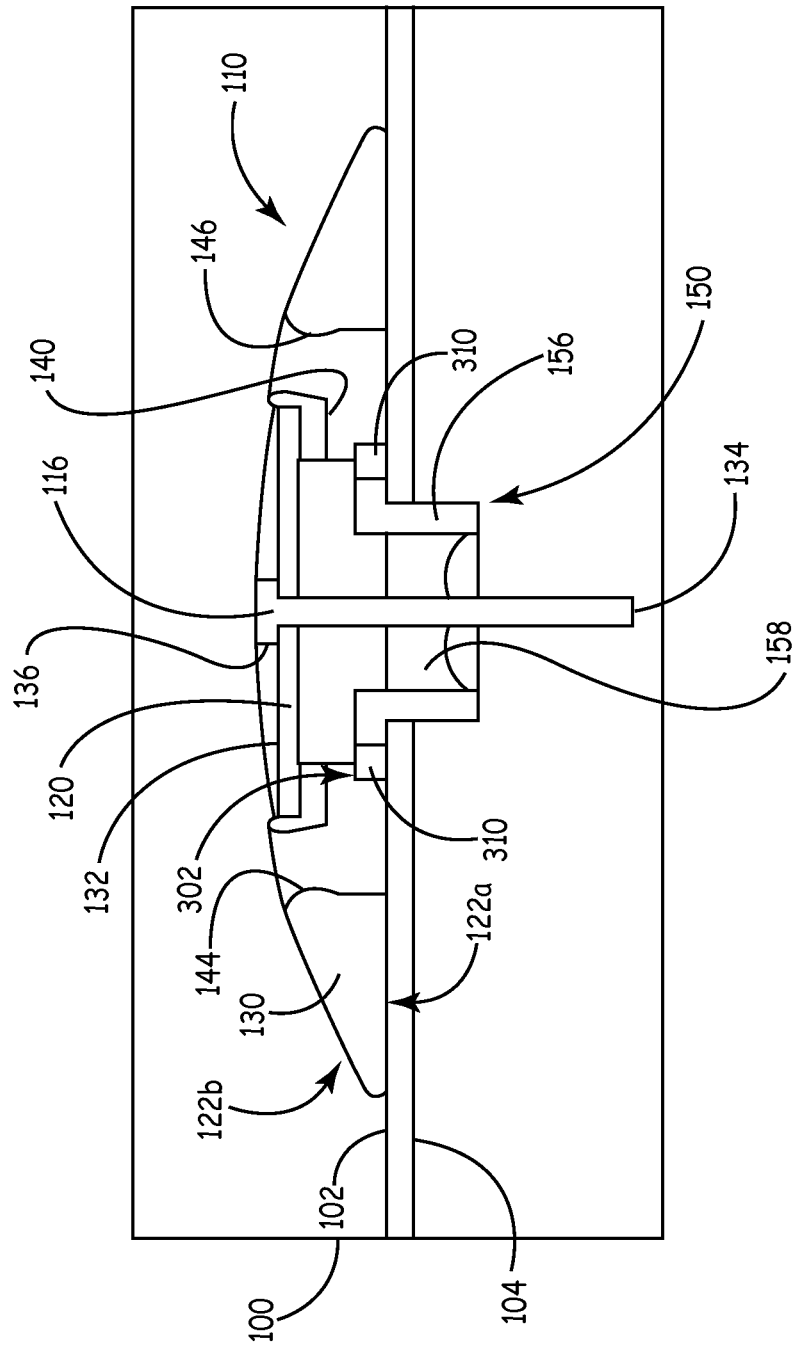
FIG. 5 is a schematic view of an electrode connected to a retention cup of FIG. 4 cutaway along lines 5-5.
Figure 6A:
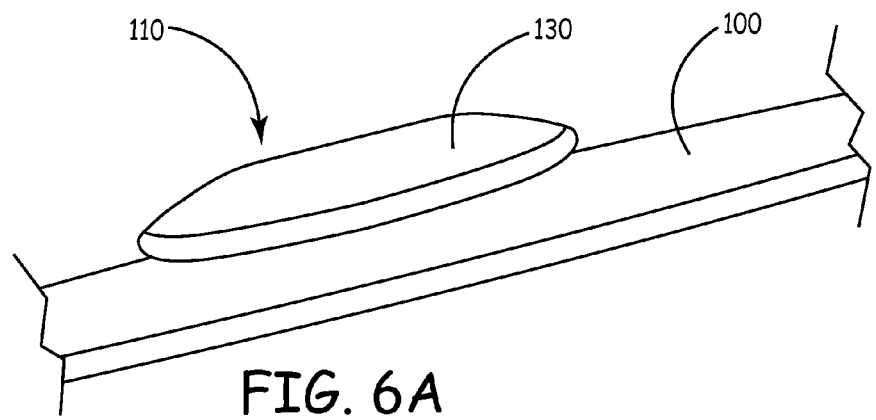
FIG. 6A is a side view of electrode connected to a retention cup.
Figure 6B:
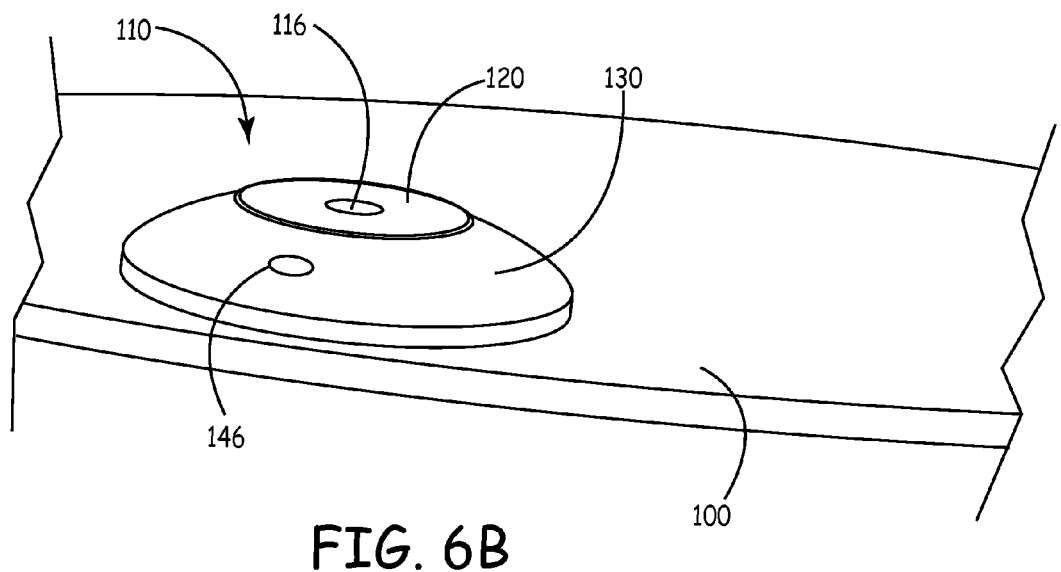
FIG. 6B is an angled top view of electrode connected to a retention cup.

Referring to FIGS. 4 and 5, feedthrough 150 serves to connect the electronic components or elements, surrounded by inner wall 104, to electrode 120 located outside outer wall 102 of housing 100. Feedthrough 150 typically comprises a feedthrough ferrule 156, a conductive wire or pin 116, and a feedthrough insulator 158. The feedthrough ferrule 156 is placed in a hole or aperture in the housing 100 that is slightly larger than the outer diameter of the main ferrule body. The ferrule 156 is then welded to the housing 100. A conductive element 116 runs through a hole in about the middle of the ferrule 156 such that an external end 136 (or T-shaped end) is coupled or connected to the electrode 120 while internal end 134 is connected to the electronics. The area between the conductive wire 116 and the ferrule 156 is filled with a hermetic insulator 158 such as glass and/or other suitable material.

Figure 7:
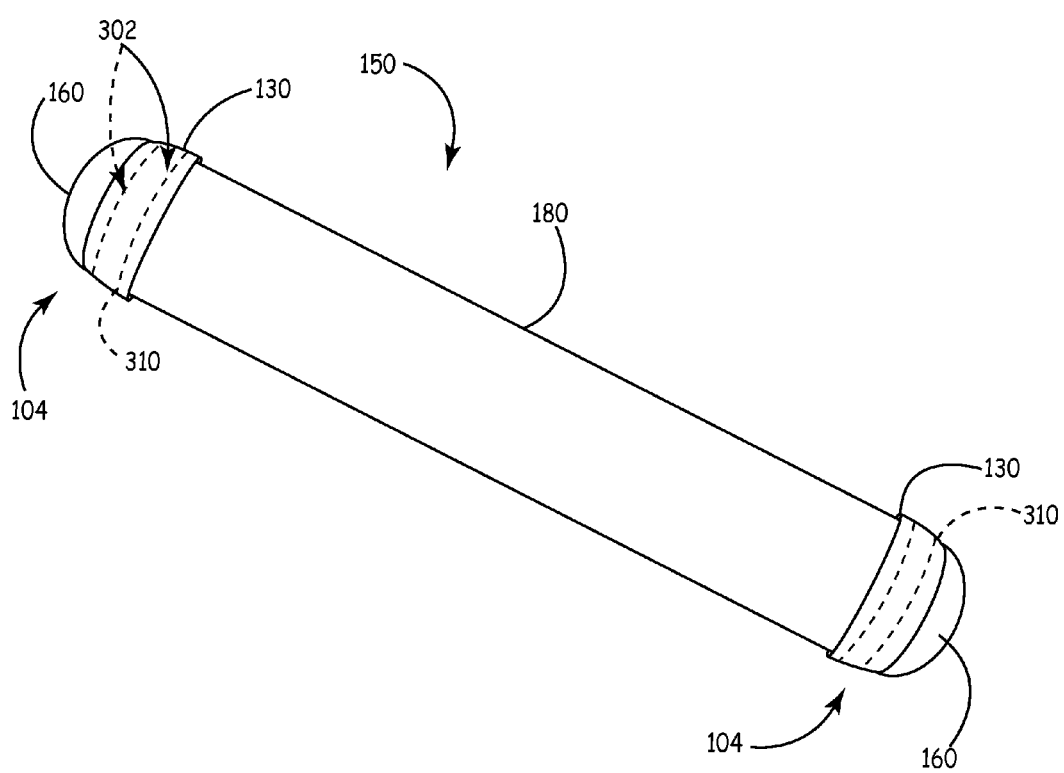
FIG. 7 is a schematic view of an implantable medical device with a dome-shaped electrode.

A securing assembly 302 supports and/or connects electrode assembly 110 to housing 100. In one or more embodiments, securing assembly 302 comprises an insulator cup 130 and a bracket 310 that are configured to conform to the housing of IMD 10, 150 and 190, respectively. For example, FIG. 7 shows that securing assembly 302 surrounds domed-shaped electrodes 160, which prevents electrodes 160 from inadvertently electrically shorting to the pill-shaped hermetic housing 180. Domed-shaped securing assembly 302 also helps push the electrodes 160 away from the housing 180 and into the patient's 12 tissue.

Details of the insulator cup 130 and the bracket 310 are depicted in FIGS. 11-14. Insulator cup 130 separates or insulates electrode 120 from housing 100. Insulator cup 130 is configured to surround an outer circumference of feedthrough 150 and extend to an outer diameter. Insulator cup 130 can be circular, dome-shaped, rectangular-shaped or another suitable shape in order to support a surface electrode. In one embodiment, the insulator cup 130 includes at least one planar side 122a (also referred to as a first side) possessing a flat or substantially flat surface for connecting with housing 100. A second side 122b such as a nonplanar side, of insulator cup 130 is exposed to body fluids.

In the embodiment depicted in FIG. 5, the insulator cup 130 preferably protrudes less than about 0.1 inches perpendicular from the housing outer wall 102 to reduce any potential discomfort for the patient. In another embodiment, the insulator cup 130 protrudes less than about 0.175 inches from the housing outer wall 102. In yet another embodiment, the insulator cup is flush with the exterior of the housing 100. The electrode 120 is aligned with the area of the housing 100 that is covered by the insulator cup 130. In other embodiments, the electrode 120 is about aligned with the area of the housing 100 that is covered by the insulator cup 130. About aligned means that the angle is 45 degrees or less between the plane that contains the perimeter of the outer electrode surface 132 and the plane that contains the perimeter of the area of the housing 100 that is covered by the insulator cup 130.

A variety of biostable insulative materials can be used to form insulator cup 130. Exemplary materials that can be used to manufacture insulator cups 130 can include polyetherimide (PEI), polyaryletheretherketone (PEEK), acrylonitrile butadiene styrene (ABS), and/or thermoplastic polyurethane (TPU); however, it should be understood that other suitable polymers can also be used. Insulator cups 130 can be manufactured by employing conventional molding or machining techniques.

Bracket 310, shown in greater detail in FIGS. 11-14, operates in conjunction with insulator cup 130 to form a securing assembly 310. Bracket 310, configured to support and/or connect the load of a surface electrode to the housing, can be Y-shaped, substantially Y-shaped, X-shaped, or other suitable shapes. Each leg 312a,b,c of bracket 310 can be integrally formed and spaced apart from each other by an angle θ. Angle θ can range from about 20 degrees to about 90 degrees. In another embodiment, angle θ can range from about 20 degrees to about 180 degrees. Typically, legs 312a,b,c are symmetrically spaced apart; however, in other embodiments, legs 312a,b,c can be asymmetrically spaced apart. In yet another embodiment, the bracket is disk shaped such that it does not include legs. The disk bracket includes a hole for the pin to pass therethrough. In yet another embodiment, the bracket is integrally formed with the housing.

In one or more embodiments, retention bracket 310 can include snap protrusions 410 that engage a retention lip 420 on the insulator cup 130. The vertical extension 430 of the retention bracket 310 is flexible such that pressing the insulator cup 130 onto the retention bracket 310 (causes the retention lip's lower surface 440 to engage the snap protrusion's chamfer 446. The interaction of the retention lip's lower surface 440 and the snap protrusion's chamfer 446 causes the vertical extension 430 to flex towards the retention bracket's center 424. Flexing towards the retention bracket's center 424 allows the retention lip 420 to move past the snap protrusion 410. Once the snap protrusions 410 are located further from the housing outer wall 102 than the retention lip 420, the snap protrusions 410 securely holds the insulator cup 130 in place because the snap protrusions 410 overhang or protrude over the retention lip 420.

The interference between the snap protrusions 410 and the retention lip 420 as the insulator cup 130 is pressed approximately downward onto the bracket 310 forces at least one of the retention bracket 310 and the insulator cup 130 to flex to allow the snap protrusions 410 to move past the retention lip 420. As mentioned above, the vertical extensions 430 can flex towards the bracket's center 424, or in other words, can flex away from the retention lip 420. When the vertical extensions 430 flex towards the bracket's center 424, the vertical extensions 430 flex approximately horizontally. In another embodiment, flexing towards the bracket's center 424 entails the vertical extension 430 rotating about its intersection with the horizontal portion of the leg 312 that abuts the outer wall 102 of the housing 100.

In another embodiment, the vertical extensions 430 do not flex and the snap protrusion's chamfer 446 forces the retention lip 420 to curl upward or expand in diameter. In yet another embodiment, the retention lip 420 has slots that allow the snap protrusion 410 to move past the retention lip 420 without requiring either the vertical extensions 430 or the retention lip 420 to flex. In this embodiment, the insulator cup 130 is rotated after the snap protrusions 410 have passed through the slots in the retention lip 420 in order to lock the insulator cup 130 in place.

Figure 14:
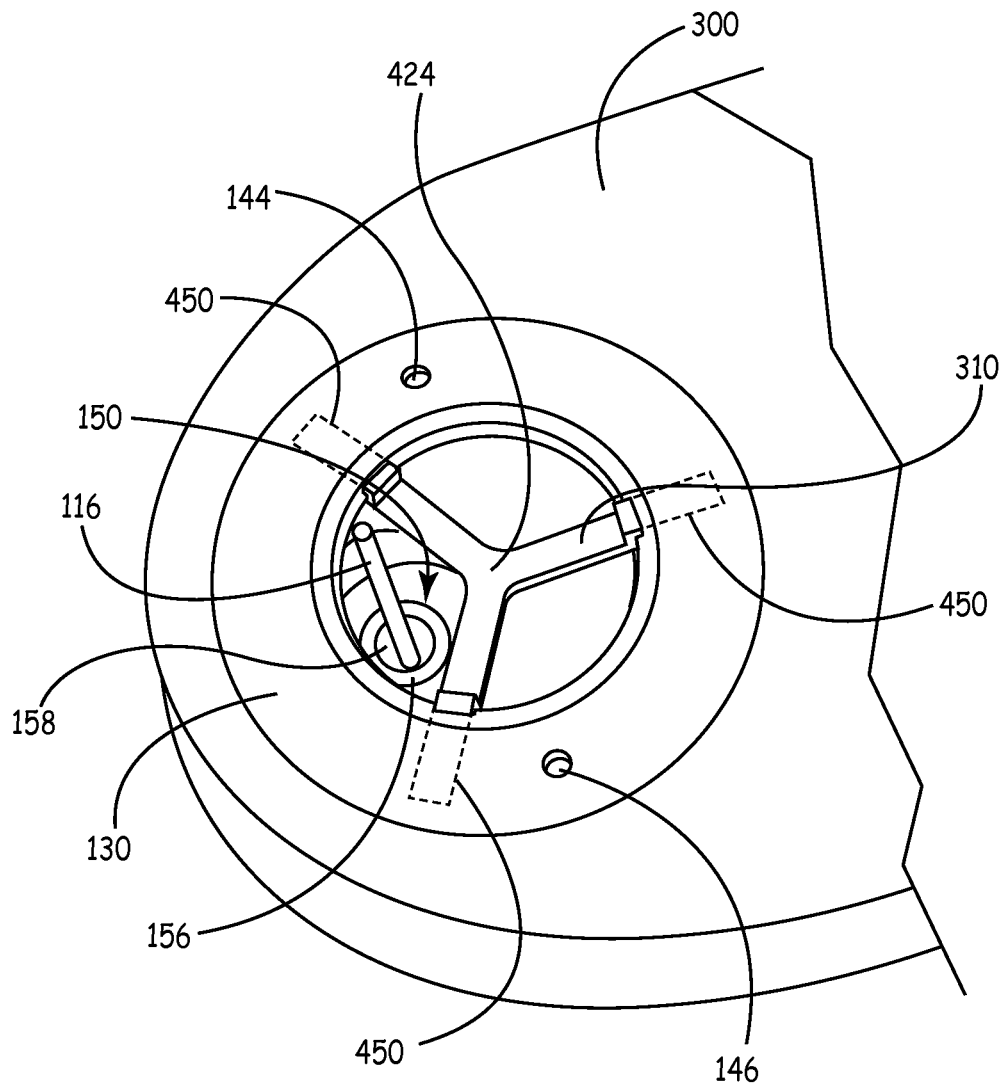
FIG. 14 depicts a schematic view of a retention bracket for supporting a surface electrode.

FIG. 14 shows an embodiment where the retention bracket 310 is insert molded into the insulator cup 130. Overmolded extensions 450 of the retention bracket 310 are fully encased within the insulator cup 130 to prevent the insulator cup 130 from moving relative to the retention bracket 310. In particular, overmolded extensions 450 of the retention bracket 310 assist insulator cup 130 to remain stationary relative to the retention bracket 310.

In one embodiment, the retention bracket 310 is manufactured by stamping the general sheet metal shape and then bending the ends of the sheet metal to form snap protrusions 410. In another embodiment, the retention bracket 310 is machined from a metal block using a multi-axis mill.

Figure 10A:
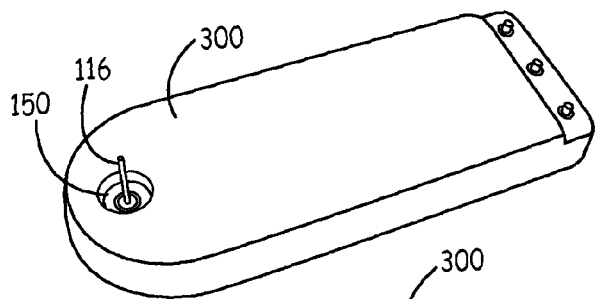
FIG. 10A is a schematic view of a narrow hermetic housing with a feed through connected thereto.
Figure 10B:
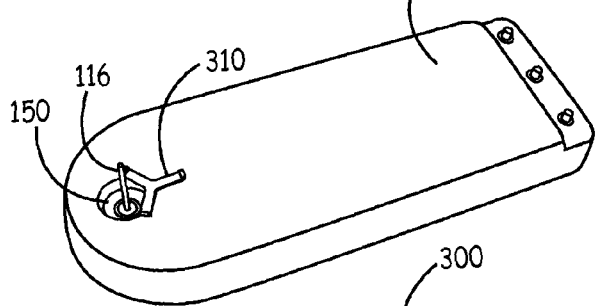
FIG. 10B is a schematic view of a retention bracket connected to the housing.
Figure 10C:
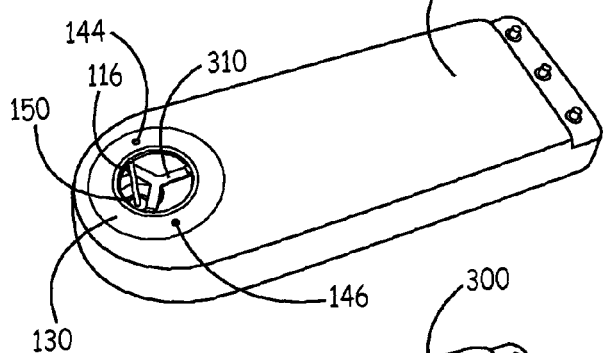
FIG. 10C depicts an insulator cup connected to the retention bracket of FIG. 10B.
Figure 10D:
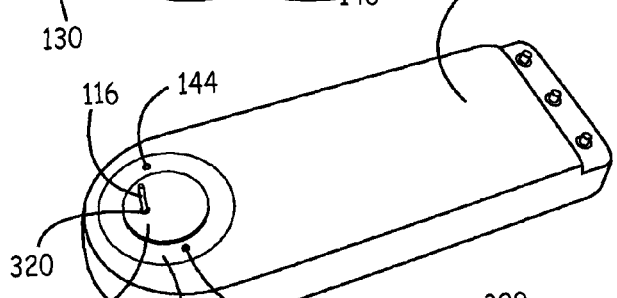
FIG. 10D depicts an electrode placed in the insulator cup of FIG. 10C.
Figure 10E:
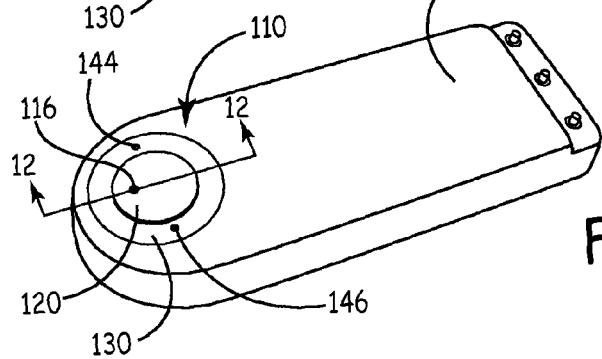
FIG. 10E depicts a conductive wire that is flush with the surface of the electrode of FIG. 10D.

FIGS. 10A-E depict various stages of manufacturing a low-profile electrode with a securing assembly 302. FIG. 10A depicts a feedthrough that has been welded into a narrow hermetic housing 300. FIG. 10B depicts a retention bracket 310 that has been connected to the narrow hermetic housing 300. For example, the retention bracket 310 can be welded to housing 100. FIG. 10C depicts an insulator cup 130 that has been snapped onto the retention bracket 310. FIG. 10D depicts an electrode 120 that has been placed in on the insulator cup 130. The conductive wire 116 extends through a small hole 320 in the electrode 120. FIG. 10E depicts a conductive wire 116 that was trimmed to be about flush with the surface of the electrode 120 and then welded to the electrode 120. Adhesive can be injected under the electrode 120 by placing the tip of the adhesive applicator in the fill hole 144. Excess adhesive is removed in a variety of ways. For example, excess adhesive can be wiped away from the electrode 120.

Figure 11:
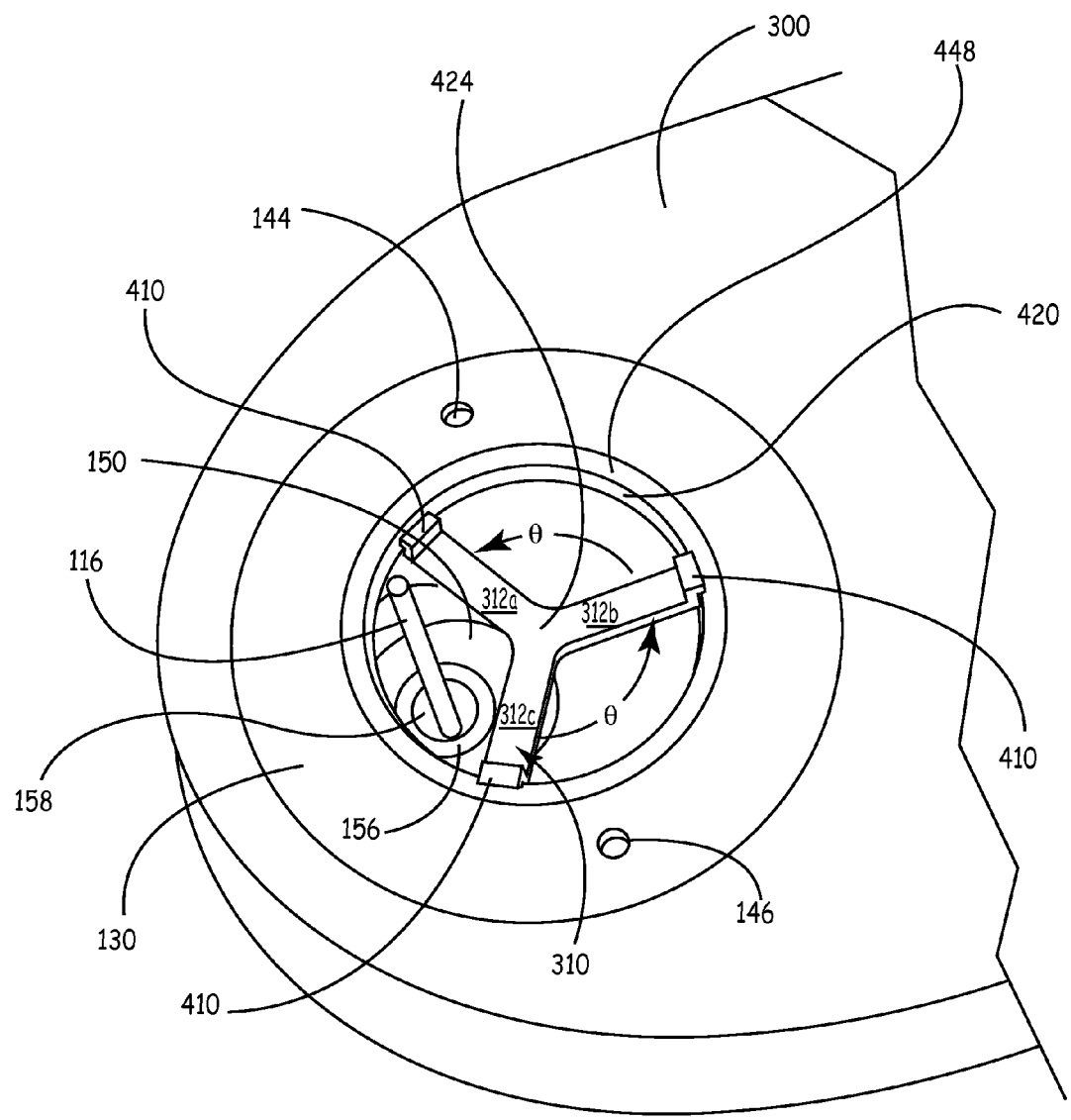
FIG. 11 depicts a top exterior view of a retention bracket connected to an electrode and housing.
Figure 12:
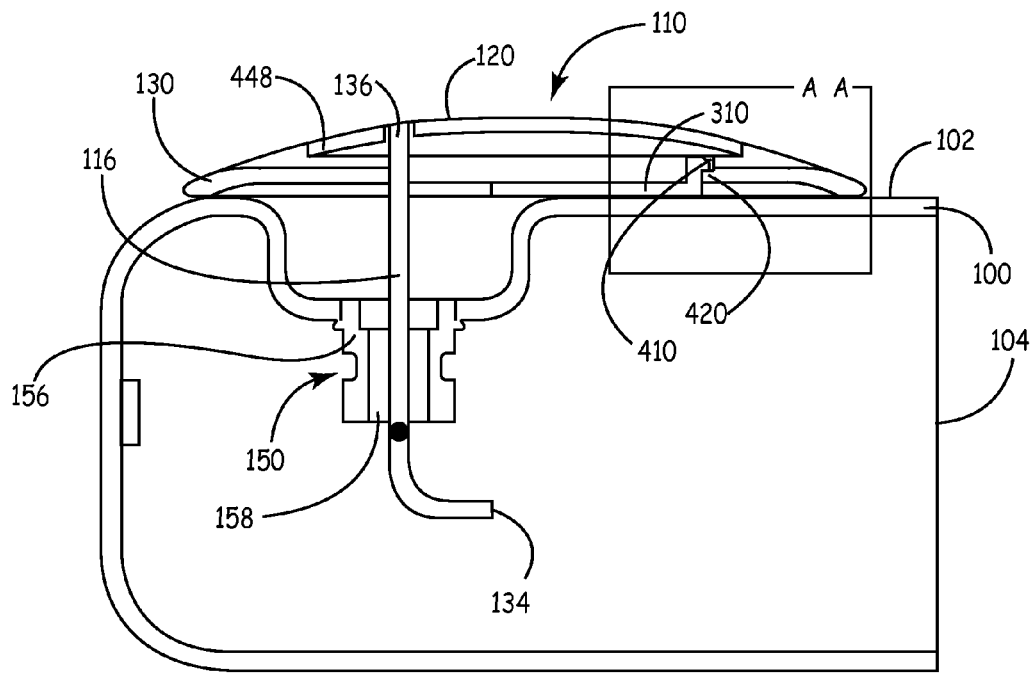
FIG. 12 depicts a cross-sectional view of a retention bracket connected to an electrode and housing.
Figure 13:
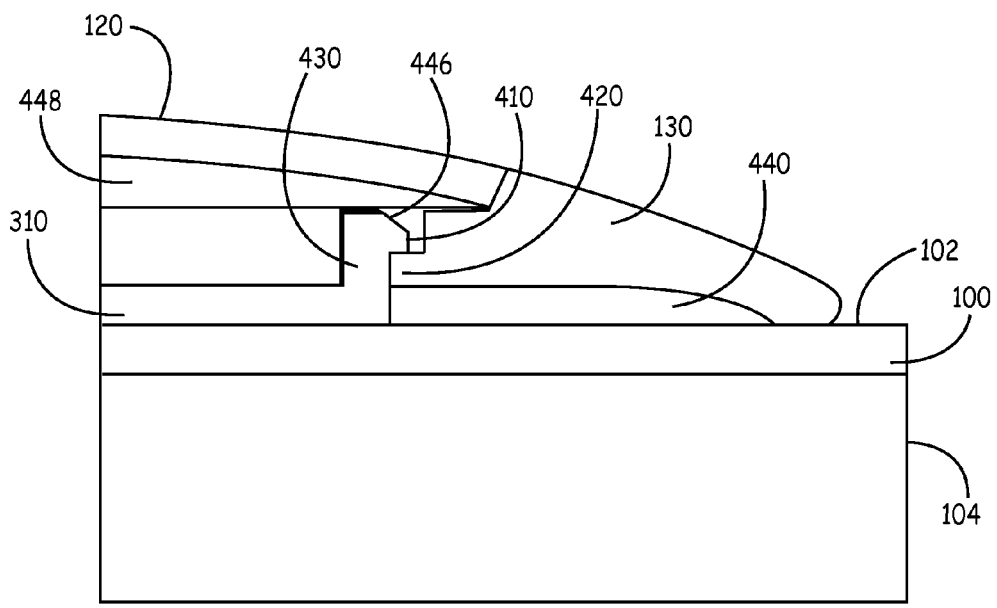
FIG. 13 depicts an enlarged view of the retention bracket connected to an electrode and housing of FIG. 12.

In the embodiment show in FIGS. 11-13, the electrode 120 resides in an indentation 448 in the insulator cup 130. Indentation 448 can help prevent the electrode 120 from moving relative to the insulator cup 130.

In other embodiments, the electrode 120 can be molded into the insulator cup 130. For example, two weld anchor features can be molded into the insulator cup 130 in addition to the electrode. The two weld anchor features (e.g. one on each side of the electrode), could be simultaneously stamped out with the electrode in a stamped lead frame. The resulting subassembly can then be insert molded. Thereafter, the stamping break-off tab could be removed to electrically isolate the weld anchors from the electrode. This process provides one insert molded part with an electrode in the center of the insulator cup, and two weld anchors, one on each side of the electrode. A hole in the electrode provides access for the feedthrough wire to pass through the electrode for welding. The weld anchors would be welded to the housing to keep the assembly securely in place.

Figure 8:
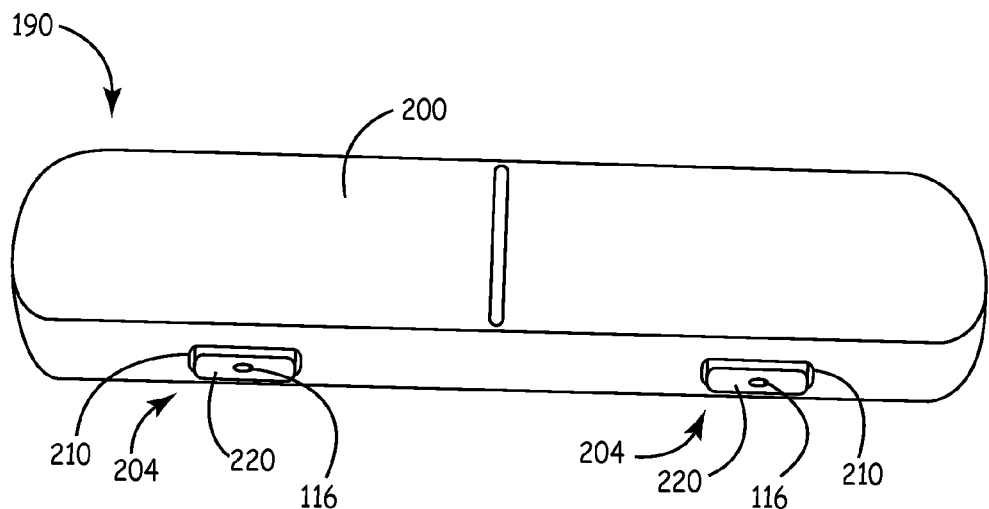
FIG. 8 depicts a schematic view of an implantable device with a rectangular hermetic housing.
Figure 9:
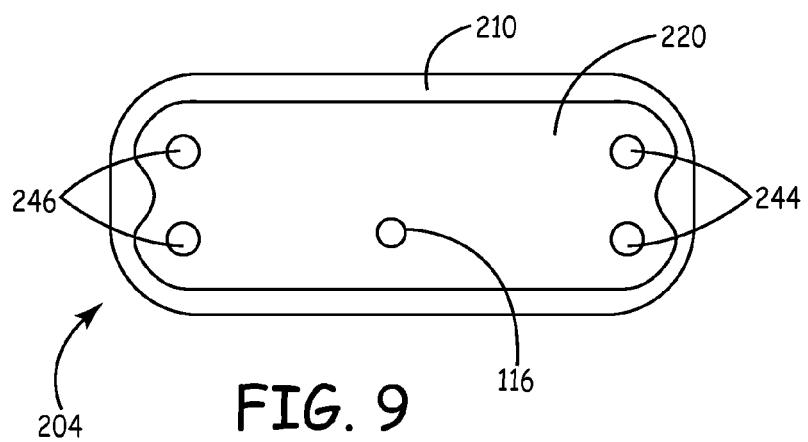
FIG. 9 depicts a low profile electrode assembly of the implantable medical device shown in FIG. 8.

FIGS. 8-9 depict still yet another securing assembly 302 for IMD 190. In this embodiment, an elongated, slender implantable device 190 includes a rectangular hermetic housing 200. Low profile rectangular electrode assemblies 204 can be located on the sides of the long, slender implantable device 190. Rectangular insulator cups 210 support rectangular electrodes 220. In this embodiment, securing assembly includes insulator cup 130 adhesively coupled to housing 100. Adhesive is injected into the fill holes 244 until adhesive 140 begins to exit vents 246 to fill the area underneath the electrode 120 that is between the insulator cup 130 and the housing 100.

FIG. 4 depicts yet another embodiment in which electrode can be further adhesively bonded to housing 100. Adhesive can be injected into the fill hole 144 until adhesive 140 begins to exit the vent 146 from filling the area underneath the electrode 120 that is between the insulator cup 130 and the housing 100. Exemplary adhesive 140 can include silicone-based medical adhesive, epoxy resin or other suitable material.

Although the present disclosure has been described in considerable detail with reference to certain disclosed embodiments, the disclosed embodiments are presented for purposes of illustration and not limitation and other embodiments of the disclosure are possible. For example, other embodiments can include ceramic brazed feedthroughs can also be used without departing from the spirit of this disclosure.

What is claimed is:

1. An implantable medical device comprising:
a housing having an inner surface and an outer surface;
electronics enclosed by the housing;
an electrode assembly coupled to the housing, the electrode assembly comprising:
  a feedthrough extending through the housing, between the inner and outer surfaces thereof, the feedthrough including a ferrule, an insulator, and an electrically conductive pin, the ferrule being coupled to the housing, the pin extending through the ferrule from an internal end thereof, adjacent the inner surface of the housing, to an external end thereof, adjacent the outer surface of the housing, the insulator filling an area between the pin and ferrule, and the internal end of the pin being coupled to the electronics;
  an electrode coupled to the external end of the conductive pin of the feedthrough; and
a securing assembly connected to the outer surface of the housing, the securing assembly including an insulator cup that surrounds a perimeter of the electrode, and a retention bracket coupled to the insulator cup and to the housing, the retention bracket extending between the outer surface of the housing and the electrode.

2. The device of claim 1, wherein the retention bracket of the securing assembly is welded to the housing.

3. An assembly for an implantable medical device, the device including electronics, a hermetically sealed housing enclosing the electronics, and a feedthrough extending through the housing, between an inner surface of the housing and an outer surface of the housing, the feedthrough including an electrically conductive pin, the pin extending from an internal end thereof, adjacent the inner surface of the housing, to an external end thereof, adjacent the outer surface of the housing, and the internal end of the pin being coupled to the electronics; and wherein the assembly comprises:
an electrode coupled to the external end of the conductive pin;
an insulator cup surrounding a perimeter of the electrode; and
a retention bracket coupled to the insulator cup and to the housing, the retention bracket extending between the outer surface of the housing and the electrode.

4. The device of claim 1, wherein the retention bracket of the securing assembly is molded into the insulator cup.

5. The device of claim 1, wherein the insulator cup of the securing assembly snaps onto the retention bracket.

6. The device of claim 1, wherein the insulator cup of the securing assembly protrudes less than about 0.175 inches perpendicular from the outer surface of the housing.

7. The device of claim 1, wherein the insulator cup of the securing assembly protrudes less than about 0.1 inches perpendicular from the outer surface of the housing.

8. The device of claim 1, wherein the securing assembly further comprises adhesive, the adhesive filling a void between the insulator cup and the outer surface of the housing.

9. The device of claim 1, wherein the electrode of the electrode assembly is non-planar.

10. The device of claim 1, wherein the electrode of the electrode assembly is dome shaped.

11. The device of claim 1, wherein the electrode of the electrode assembly is rectangular.

12. The device of claim 1, wherein the electrode of the electrode assembly has a high-surface area coating.

13. The device of claim 1, wherein the insulator cup of the securing assembly includes an indentation in which the electrode resides.

14. The device of claim 1, wherein the securing assembly includes at least one adhesive fill hole or vent.

15. The assembly of claim 3, further comprising at least one adhesive fill hole or vent.

16. The assembly of claim 3, wherein the retention bracket is welded to the housing.

17. The assembly of claim 3, wherein the retention bracket is molded into the insulator cup.

18. The assembly of claim 3, wherein the insulator cup snaps onto the retention bracket.

19. The assembly of claim 3, wherein the insulator cup protrudes less than about 0.175 inches perpendicular from the outer surface of the housing.

20. The assembly of claim 3, wherein the insulator cup protrudes less than about 0.1 inches perpendicular from the outer surface of the housing.

21. The assembly of claim 3, further comprising adhesive, the adhesive filling a void between the insulator cup and the outer surface of the housing.

22. The assembly of claim 3, wherein the electrode is non-planar.

23. The assembly of claim 3, wherein the electrode is dome shaped.

24. The assembly of claim 3, wherein the electrode is rectangular.

25. The assembly of claim 3, wherein the electrode has a high-surface area coating.

26. The assembly of claim 3, wherein the insulator cup includes an indentation in which the electrode resides.

27. The assembly of claim 3, wherein the retention bracket includes radially extending legs, between which the conductive pin extends.

28. The assembly of claim 3, wherein the retention bracket is disk shaped and includes a hole through which the conductive pin extends.

\* \* \* \* \*